(12) United States Patent
Bertoch

(10) Patent No.: US 10,406,358 B1
(45) Date of Patent: Sep. 10, 2019

(54) CHRONIC PAIN TREATMENT DEVICE

(71) Applicant: Todd M. Bertoch, Prescott, AZ (US)

(72) Inventor: Todd M. Bertoch, Prescott, AZ (US)

(*) Notice: Subject to any disclaimer, the term of this patent is extended or adjusted under 35 U.S.C. 154(b) by 93 days.

(21) Appl. No.: 15/494,686

(22) Filed: Apr. 24, 2017

(51) Int. Cl.
| | |
|---|---|
| *A61N 1/36* | (2006.01) |
| *A61N 1/04* | (2006.01) |
| *A61N 1/32* | (2006.01) |
| *A61M 37/00* | (2006.01) |
| *A61F 7/00* | (2006.01) |
| *A61N 1/08* | (2006.01) |

(52) U.S. Cl.
CPC .......... *A61N 1/36021* (2013.01); *A61F 7/007* (2013.01); *A61M 37/00* (2013.01); *A61N 1/0492* (2013.01); *A61N 1/08* (2013.01); *A61N 1/325* (2013.01); *A61M 2037/0007* (2013.01); *A61M 2205/52* (2013.01); *A61M 2205/8206* (2013.01)

(58) Field of Classification Search
CPC .......... A61N 1/0456; A61N 1/18; A61N 1/20; A61N 1/205; A61N 1/30; A61N 1/36; A61N 1/36014; A61N 1/36021; A61N 1/36182; A61N 1/0492; A61N 1/08; A61N 1/325; A61F 7/007; A61M 37/00; A61M 2037/0007; A61M 2205/52; A61M 2205/8206
See application file for complete search history.

(56) References Cited

U.S. PATENT DOCUMENTS

| | | | | |
|---|---|---|---|---|
| 4,619,252 | A | 10/1986 | Ibbott | |
| 5,336,255 | A * | 8/1994 | Kanare | A61N 1/0452 607/112 |
| 5,601,618 | A * | 2/1997 | James | A61F 7/007 607/148 |
| 6,256,533 | B1 * | 7/2001 | Yuzhakov | A61M 37/0015 604/20 |
| 6,477,410 | B1 * | 11/2002 | Henley | A61N 1/0428 601/1 |
| 6,520,950 | B1 * | 2/2003 | Hofmann | A61N 1/0412 604/503 |
| 7,860,571 | B2 | 12/2010 | Pollock | |
| 2001/0027066 | A1 * | 10/2001 | Loh | H01R 13/514 439/701 |
| 2004/0267189 | A1 * | 12/2004 | Mavor | A61N 1/044 604/20 |
| 2007/0073356 | A1 * | 3/2007 | Rooney | A61N 1/0531 607/46 |
| 2013/0280692 | A1 * | 10/2013 | Gourlay | A61M 1/1698 435/1.2 |

(Continued)

*Primary Examiner* — Nathan R Price
*Assistant Examiner* — John A Doubrava
(74) *Attorney, Agent, or Firm* — Harpman & Harpman

(57) ABSTRACT

A device to relieve pain in the body of humans by inducing a controlled positive/negative electric charge at the painful site. Providing enhanced transport and targeted delivery of pain relieving classifications of drugs including nonsteroidal anti-inflammatory drugs (NSAID) and steroid drug compounds (corticosteroids), and important intrinsic anti-inflammatory agents. A shielded transmission electrode applies alternating positive and/or negative charge stimulating or repressing the enhanced delivery or repression of drugs to the injury site for increased therapeutic treatment dependent on known therapeutic properties of so prescribed drugs inputted to a charge generating micro-controller.

2 Claims, 3 Drawing Sheets

(56) References Cited

U.S. PATENT DOCUMENTS

2014/0249601 A1* 9/2014 Bachinski .......... A61N 1/37217
607/59
2016/0184612 A1* 6/2016 Desimone ................ A61N 5/10
600/431

* cited by examiner

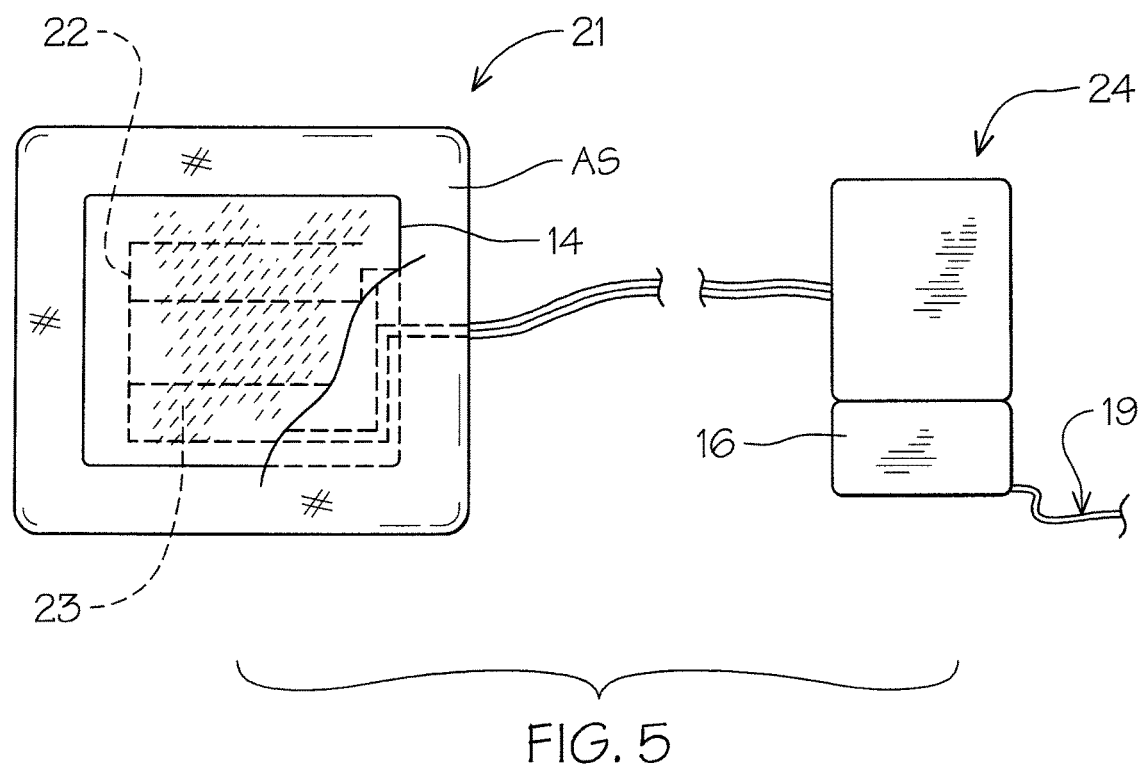

CHRONIC PAIN TREATMENT DEVICE

BACKGROUND OF THE INVENTION

1. Technical Field

The present invention relates to pain relieving devices and more specifically the use of electrical stimulus in combination with pain relief therapeutic drugs to significantly enhance their efficacy and diminish their side effects.

Pain is a complex multi-factorial disorder that is typically treated with a variety of narcotic medications with the inherent risk of opiate addiction and its accompanying staggering societal costs. While many factors contribute to acute and chronic pain, most consistent is the presence of inflammation at the site of pain generation.

Nonsteroidal anti-inflammatory drugs (NSAIDS) have proven remarkably effective in the treatment of both acute and chronic pain, with many studies showing equivalent efficacy of NSAIDS and narcotics without the risks of the side effects and addiction associated with narcotic use. Unfortunately, serious, even life-threatening side effects limit the use of NSAIDS in many patient populations.

After administration, NSAIDS are absorbed into the bloodstream where they are bound to plasma proteins which carry the drug molecules throughout the circulatory system. The molecules are removed from their carrier proteins and deposited indiscriminately throughout the tissues of the body by a process of competitive binding. The very small percentage of NSAID molecules actually deposited at the site of inflammation then act to diminish the inflammatory process resulting in relief of pain. Side effects occur when these molecules are deposited within, and affect tissues and organ systems not associated with the acute or chronic pain syndrome.

Intrinsic inflammatory mediators known as cytokines are responsible for the body's natural moderation of inflammation at acute and chronic pain sites and these have unique biochemical properties. Pro inflammatory cytokines and anti-inflammatory cytokines have competing effects at the inflammation site.

The most potent pro inflammatory cytokines are interleukin-1 beta (IL-1B), interleukin-6 (IL-6) and tissue necrosis factor-alpha (TNF-a). The evidence indicates that these cytokines are involved in the process of pathological pain along with anti-inflammatory cytokines, the most important of which is interleukin-10 (IL-10).

The proteins and compounds described above have a particular biochemical attribute which the present invention intends to exploit—their corresponding electrical charge. Specifically, NSAID protein carriers possess a significant negative electrical charge in the serum. The principal pro-inflammatory cytokines (IL-1B, IL-6, and TNF-α) are negatively charged as well. Correspondingly, the most important anti-inflammatory cytokine (IL-10) tends to be positively charged in the bloodstream.

2. Description of Prior Art

Prior art devices have been developed for the relief of pain and to promote fast healing in humans. Such devices use electrical stimulation, typically having a positive charge induction pad and a negative charged pad developing an electrical field there between to flow through the location of the injury, see for example U.S. Pat. No. 7,860,571 as a pain-relieving device.

U.S. Pat. No. 4,619,252 is directed to a therapeutic method for using a sheet like battery. A negative electrode of the battery is attached to the skin with a covering member over the positive electrode causing an electrical current to flow through the afflicted skin of the site.

SUMMARY OF THE INVENTION

A therapeutic device for the treatment of acute and chronic pain by controlling, enhancing and targeting the delivery of pain relieving compounds into specific pain generating tissue following oral, intravenous or intramuscular administration of the drug. A programmable electric charge stimulation device provides regulated sequential positive and negative electric charges to the site of inflammation from a single distribution pad using and exploiting a particular biochemical attribute of the plasma proteins by their electrical charge.

DESCRIPTION OF THE DRAWINGS

FIG. 5 is a composite bottom plan view of an alternate electrical application patch with heating and cooling application inserts and support generator.

DETAILED DESCRIPTION OF THE INVENTION

A pain treatment device 10 of the invention is used in conjunction with the administration of pain relieving (PR) compounds, specifically, but not limited to non-narcotic therapies such as nonsteroidal anti-inflammatory drugs (NSAIDS) that provide well documented analgesic and anti-inflammatory effects as potent pain relievers. The pain treatment device 10 provides the ability to regulate the effective delivery of the pain-relieving compounds by introducing a positive or negative charge, as needed, which takes advantage of the known electrical charge properties of the chemical compounds prescribed.

It is the goal of the pain treatment device 10 to increase the delivery and subsidence as determined of NSAID molecules specifically to the tissue where the chronic pain is generated by the controlled regulated selective application of low voltage positive and negative electrical charges, decreasing both total drug dose requirements and the dangerous side effects of said drugs in other tissues and organ systems.

Figure 1:
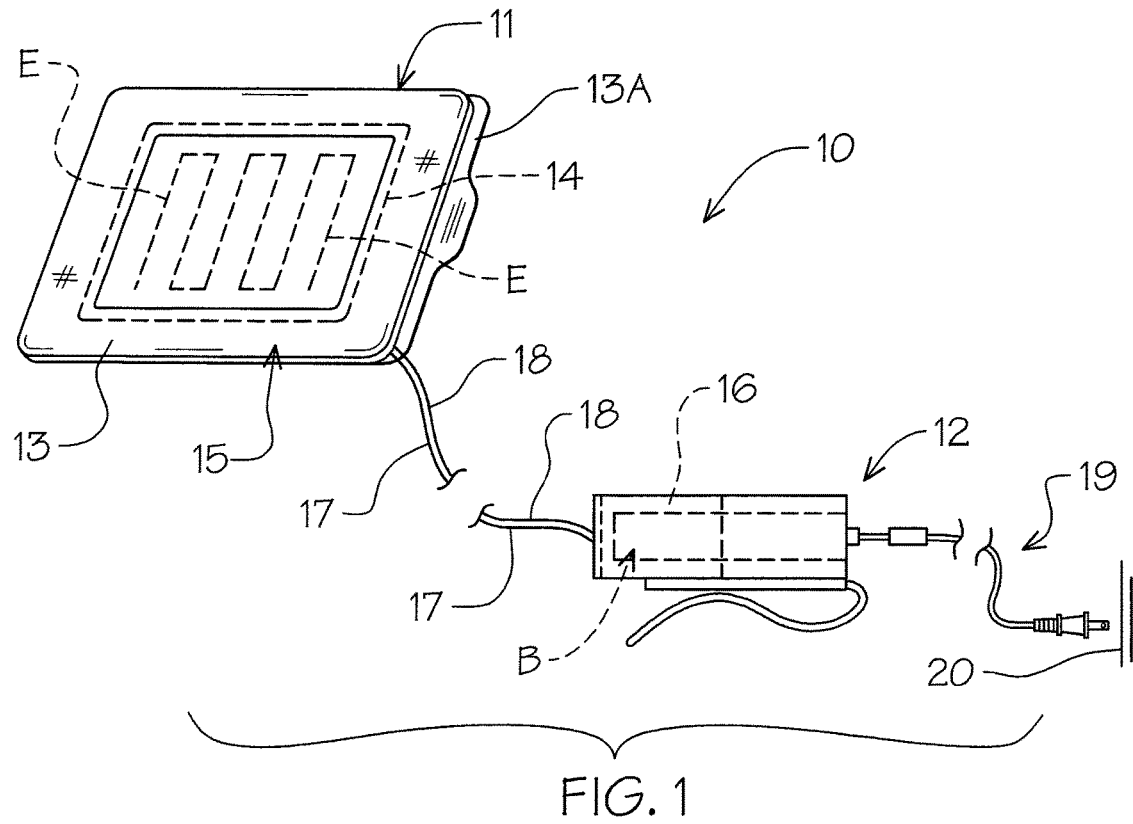
FIG. 1 is a composite perspective illustrative view of the pain treatment device of the invention.
Figure 2:
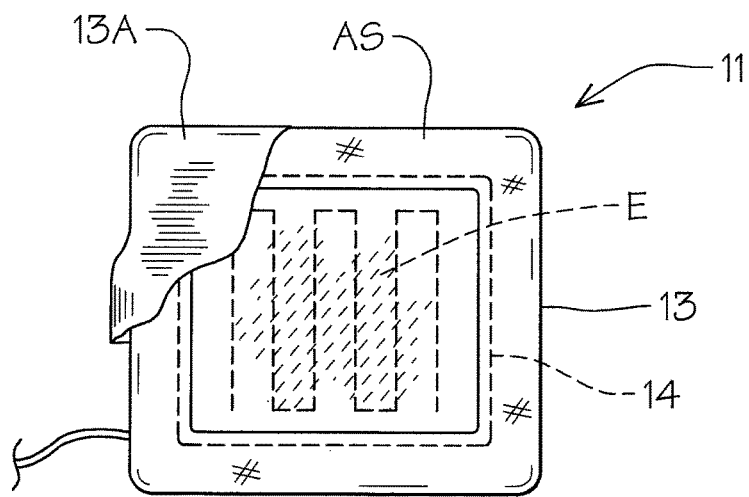
FIG. 2 is a bottom plan view of the application electrode application patch of the device.
Figure 3:
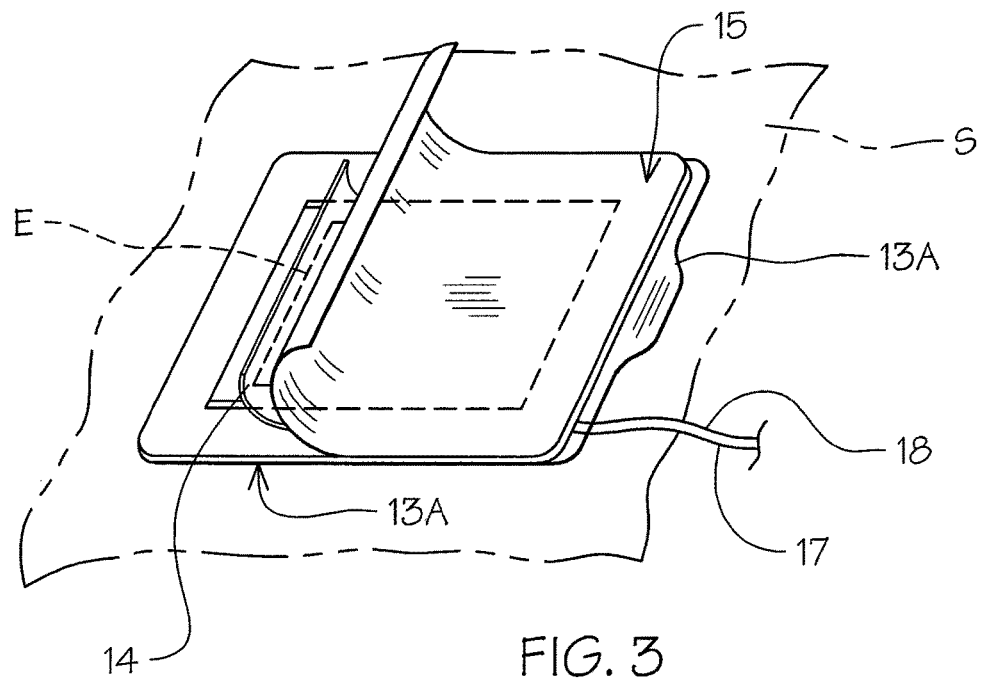
FIG. 3 is a partially expanded perspective view of the electrical application patch.

The pain treatment device 10 can be seen in FIG. 1 of the drawings having an electrical transmission application pad 11 and remote power source 12. The electrical transmission pad 11, in this example has an adhesive release 13A mounting support sheet 13 with a centrally positioned electrodes E in a mat configuration 14 which is shielded with a non-conductive cover 15 and positioned so as to be placed directly on the skin S as seen in FIG. 3 of the drawings.

The electrical transmission application pad 11 is held in place by the exposed contact adhesive surface AS surrounding the electrode mat 14 which may be of various well known and developed designs conventionally available capable of providing a safe and effective contact of the skin when applying a low voltage electric current as will be described in detail hereinafter.

An electrical charge generator and combined micro-controller 16 having a programmable logic data chip set, is in electrical communication with the electrical transmission application pad 11 and a source of power P by interlinking cables 17 and 18. In the primary basic form of the invention, the charge generator and controller 16 provides both a positive and negative low voltage electric charge to the electrical transmission application pad 11 as determinately required. The power source, in this example, is illustrated as a rechargeable battery B with a power plug and line assembly 19 for recharging with access to a standard 110 Volt AC power outlet 20 illustrated generally.

The rechargeable battery B therefore allows effective portability to the electric transmission application pad 11 allowing for extended remote usability between charges as will be well understood by those skilled in the art.

The micro-controller 16 of the charge generator provides a variety of positive and negative charge duration cycles dependent on the applied pain regulating compound used and entered to said programmable logic data chip set as will be described hereinafter of charge value duration and efficiency drive therefrom within the scope of the invention.

In an application example, after administration of an NSAID, a strong positive electric field is generated in the transmission application pad 11 through the micro-controller 16. As the NSAID molecules are absorbed into the bloodstream, they are bound to plasma proteins and carried via the circulatory system. It is believed that applying the positive charge produces an attractive force on the negatively charged plasma proteins transporting the NSAID molecules slowing the transit of the NSAID protein complex thereby concentrating the NSAID molecules in the pain generating tissue.

It will be seen that the increased duration so initiated at the site of inflammation will increase the likelihood that quantitatively more NSAID will be displaced from the protein by competitive binding and therefore be delivered directly into the tissue where the inflammation is occurring as opposed to a non-charged aided application well known and understood within the prior art.

Based on the known published prior art guidelines, the given calculated peak plasma concentration and half-life data of the specific NSAID administered at a specific time is entered via data chip set determines and the polarity of the transmission application pad 11 is reversed to a negative charge. The negative charge will therefore correspondingly attract the positive charge anti-inflammatory cytokines to the pain induced area while simultaneously repelling the negatively charged pro inflammatory cytokines.

It is evident that this combination of induced varied polarization charges will increase NSAID delivery exactly to the site of inflammation and decrease the pro inflammatory and correspondingly increase of anti-inflammatory cytokines at the pain stimulation tissue in a novel method of focused NSAID delivery heretofore unachieved.

The advantages include decreased required dosage for NSAID therapy, expanding the population of patients eligible for treatment and reducing induced side effects, thereby avoiding the use of narcotic medications for chronic pain and its associated addictive issues.

It will be evident from the above description that given the treatment properties, a broadened use criteria is available including, for example, steroid compounds, specifically corticosteroids, which are potent anti-inflammatory agents transported in the blood by a transport protein (transcortin) which carries a negative charge in the serum and thus will be subjected to the same therapeutic methodology with a similar optimum treatment properties as hereinbefore described.

Referring now to FIG. 5 of the drawings, an alternate form of the invention can be seen wherein a modified application pad 21 is illustrated having a heating and cooling component 22 and 23 and generator component 24 illustrated graphically. It is well understood that the application of topical heat component 22 will dilate the surrounding blood vessels thus increasing blood flow to the heated tissue. It can therefore be determined that by combining local heating with the induced positive electrical charge at the site of pain generation, targeted delivery of the pain relieving medications can be further enhanced.

Conversely, it will be seen that between drug doses when, as noted, the polarity of the transmission application pad 11 is reversed the cooling component 23 is employed as a well-known natural anti-inflammatory modality, thus the vasoconstriction and decreased blood flow would be timed to proceed when the administered levels of the drug are already low, avoiding drug delivery issues.

Heating and cooling component properties of the enhanced electro-charge combination transmission application pad 21 can rely on well-known induced electrical heating methods as well as known state of the art solid state cooling devices, both of which require additional support module 25 remotely connected to the enhanced heating/cooling and manipulative charge delivery pad 26 of the alternate form.

As noted, a micro controller 16 will be programmed with regards to specific known and prescribed treatment drugs and corresponding dosage, timing activation table data to match the administration thereof.

Figure 4:
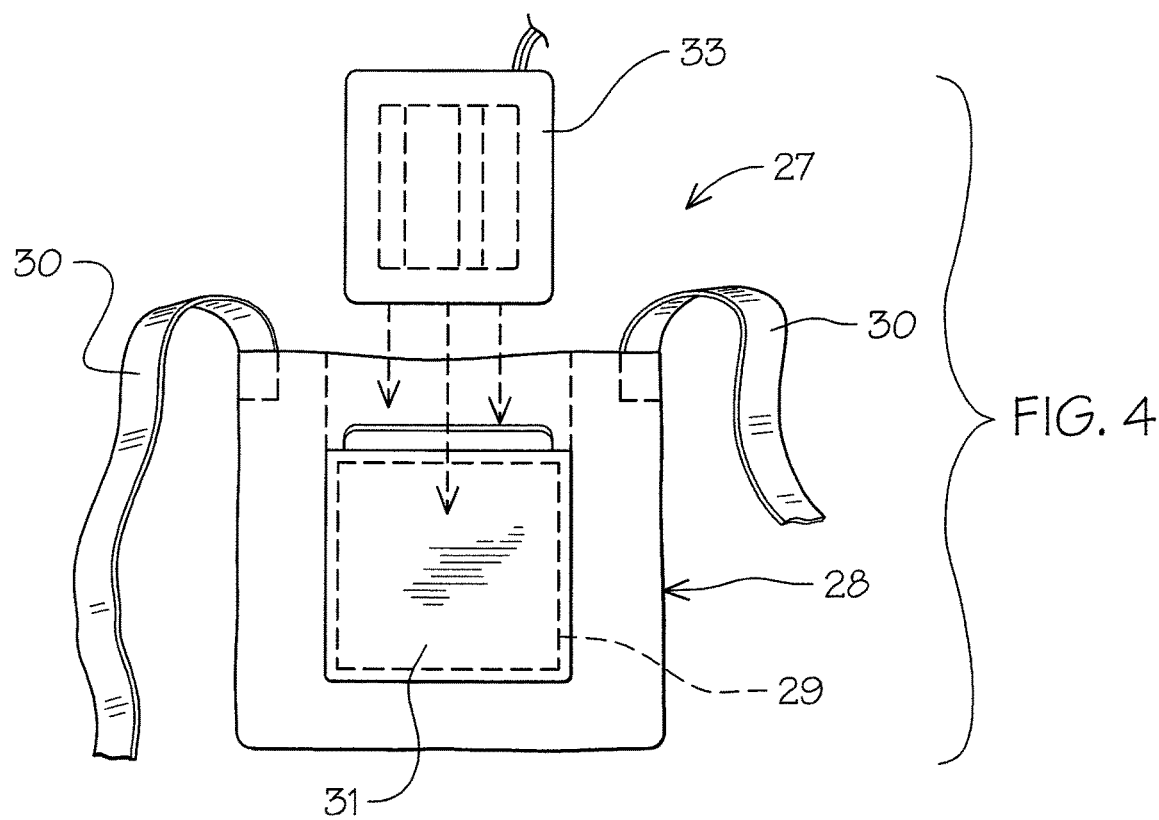
FIG. 4 is a top plan view of an alternate electrical application patch configuration.

Referring to FIG. 4 of the drawings, an alternate application pad 27 can be seen wherein a reusable securing support assembly 28 can be seen having an application change pad pocket 29 on one side, shown in broken lines, with multiple extending patient attachment straps 30. A support pocket 31 provides for a battery supply 32 allowing the application pad to be selectively and removably attached and reused on a patient. An electrical charge pad 33 has the same electrode position and charge inducing potential as that of the primary form of the invention with the potential for alternate administration of heating and cooling components as hereinbefore described removably positioned in the change pad pocket 29. It will thus be seen that a new and novel pain relieving apparatus has been described and it will be apparent to those skilled in the art that various changes and modifications may be made without departing from the spirit of the invention.

Therefore I claim:

1. A method of relieving pain by combining cycled application of positive and negative voltage electric power to a site of inflammation with administration of pain relieving medications comprising the steps of;
   a. administering a prescribed dosage of at least one pain relieving medication[s] from a group including: non-steroid anti-inflammatory drugs (NSAID's) and corticosteroids to a patient;
   b. inputting a therapeutic time duration of said pain relieving medication to a selective electronic charge generating controller in communication with a source of voltage electrical power;
   c. providing an electrical charge conductive pad, having an exposed electrical conductive material;

d. connecting said electrical conductive material to said selective electrical charge generating controller;
e. providing an electrically insulated charge transmission pad having isolated area of exposed conductive material;
f. contacting said exposed conductive material to skin of a patient;
g. applying a positive then a negative electrical charge to said exposed conductive material from the selective electronic charge generating controller and a source of electrical power;
h. selectively generating a positive then negative electrical field about said exposed electrical conductive material isolated at the site of inflammation on said patient corresponding to the proscribed medication therapeutic duration,
i. said positive electrical field providing an attractive force on said at least one pain relieving medication transporting negatively charged plasma proteins within blood of a patient; slowing transit of protein complexes of said at least one pain relieving medication; increasing duration of protein complexes of said at least one pain relieving medication at a source of inflammation; and concentrating molecules of said at least one pain relieving medication in pain source generating tissue,
j. said negative electric field providing an attractive force on positively charged anti-inflammatory cytokines to said site of inflammation; repelling negatively charged pro-inflammation cytokines; and increasing said at least one pain relieving medication delivery to said site of inflammation.

2. The method of reducing pain set forth in claim 1 wherein said source of electrical power comprises;
a rechargeable battery and a primary power source.

* * * * *